(12) United States Patent
Sinbar et al.

(10) Patent No.: US 8,586,928 B2
(45) Date of Patent: Nov. 19, 2013

(54) THERMOGRAPHY BASED SYSTEM AND METHOD FOR DETECTING COUNTERFEIT DRUGS

(75) Inventors: Eran Sinbar, Karmiel (IL); Yoav Weinstein, Atlit (IL)

(73) Assignee: Semi-Conductor Devices—An Elbit Systems-Rafael Partnership, Haifa (IL)

( * ) Notice: Subject to any disclaimer, the term of this patent is extended or adjusted under 35 U.S.C. 154(b) by 536 days.

(21) Appl. No.: 12/672,593

(22) PCT Filed: Aug. 7, 2008

(86) PCT No.: PCT/IL2008/001088
§ 371 (c)(1),
(2), (4) Date: May 24, 2010

(87) PCT Pub. No.: WO2009/019698
PCT Pub. Date: Feb. 12, 2009

(65) Prior Publication Data
US 2012/0012750 A1    Jan. 19, 2012

(30) Foreign Application Priority Data
Aug. 8, 2007  (IL) .......................................... 185130

(51) Int. Cl.
*G01N 21/95*  (2006.01)
(52) U.S. Cl.
USPC ....................................................... 250/340
(58) Field of Classification Search
CPC ................................................ G01N 21/9508
USPC ........................................................ 250/340
See application file for complete search history.

(56) References Cited

U.S. PATENT DOCUMENTS

| 4,795,906 A | 1/1989 | Adams et al. |
| 4,965,451 A | 10/1990 | Solter |
| 6,224,699 B1 | 5/2001 | Bett et al. |
| 6,316,772 B1 | 11/2001 | Egelberg |

(Continued)

FOREIGN PATENT DOCUMENTS

| CA | 2 267 586 A1 | 10/1999 |
| CN | 2661526 | 12/2004 |

(Continued)

OTHER PUBLICATIONS

Gergenova Z.V., et al., "Infrared Thermographic Nondestructive Testing System". XI Modern Technique and Technologies 2005, pp. 182-183, (XP031244843).

(Continued)

*Primary Examiner* — Constantine Hannaher
(74) *Attorney, Agent, or Firm* — Frommer Lawrence & Haug LLP; William S. Frommer

(57) ABSTRACT

A system and a method for determining the authenticity of a pharmaceutical product. The product is actively cooled to a temperature below ambient temperature. One or more thermographic IR images of the product are acquired in a wavelength or wavelength spectrum selected from the mid wave IR (MWIR) to very long wave IR (VLWIR) spectrum. At least one of the images is acquired while the temperature of the product is below ambient temperature. The acquired one or more images of the product or a quantified value deduced therefrom are compared with a signature of a reference drug. The comparison is displayed, thereby enabling determination of the authenticity of the product.

15 Claims, 15 Drawing Sheets

(56) References Cited

U.S. PATENT DOCUMENTS

| | | |
|---|---|---|
| 6,395,538 B1 | 5/2002 | Naughton et al. |
| 6,541,271 B1 | 4/2003 | McFarland et al. |
| 6,771,369 B2 | 8/2004 | Rzasa et al. |
| 6,853,447 B2 | 2/2005 | Goetz |
| 7,006,214 B2 | 2/2006 | Rzasa et al. |
| 7,028,723 B1 | 4/2006 | Alouani et al. |
| 7,046,359 B2 | 5/2006 | Voigt et al. |
| 7,126,685 B1 | 10/2006 | Paige et al. |
| 7,218,395 B2 | 5/2007 | Kaye et al. |
| 7,317,526 B2 | 1/2008 | Voigt et al. |
| 7,364,696 B1 | 4/2008 | Sarvazyan |
| 7,434,986 B2 | 10/2008 | Ignatowicz |
| 7,462,809 B2 | 12/2008 | DiMarzio et al. |
| 2004/0021861 A1 | 2/2004 | Lewis et al. |
| 2004/0135086 A1 | 7/2004 | Lewis et al. |
| 2005/0108044 A1 | 5/2005 | Koster |
| 2005/0169511 A1 | 8/2005 | Jones |
| 2005/0243305 A1 | 11/2005 | Vig et al. |
| 2005/0276907 A1 * | 12/2005 | Harris et al. .............. 427/8 |
| 2005/0286606 A1 | 12/2005 | Ignatowicz |
| 2006/0289766 A1 | 12/2006 | DiMarzio et al. |
| 2007/0118324 A1 | 5/2007 | Gulati |
| 2008/0022632 A1 | 1/2008 | Gysi et al. |
| 2008/0197284 A1 | 8/2008 | Ebenstein et al. |
| 2012/0013734 A1 | 1/2012 | Ranieri et al. |

FOREIGN PATENT DOCUMENTS

| | | |
|---|---|---|
| DE | 196 29 101 A1 | 1/1998 |
| DE | 199 08 410 A1 | 5/2000 |
| EP | 1 560 009 A1 | 8/2005 |
| JP | 8-184571 | 7/1996 |
| JP | 09 297114 | 11/1997 |
| JP | 2002 211058 | 7/2002 |
| JP | 2003-307505 | 10/2003 |
| JP | 2005 526998 | 9/2005 |
| WO | WO 96/18978 | 6/1996 |
| WO | WO 00/67204 | 11/2000 |
| WO | WO 03/100714 A1 | 12/2003 |
| WO | WO 2005/040739 | 5/2005 |
| WO | WO 2006/090353 A1 | 8/2006 |
| WO | WO 2008/021520 | 2/2008 |
| WO | WO 2009/019698 | 2/2009 |
| WO | WO 2010/120555 | 10/2010 |

OTHER PUBLICATIONS

Bechard, Simon R. et al., "Infrared Imaging of Pharmaceutical Materials Undergoing Compaction". Pharmaceutical Research, vol. 9, No. 4, 1992, pp. 521-528. XP008077451.

Puchert, T. et al. "Near-infrared chemical imaging (NIR-CI) for counterfeit drug identification—A four-stage concept with a novel approach of data processing (Linear Image Signature)". Journal of Pharmaceutical and Biomedical Analysis, vol. 51, Issue 1, Jan. 5, 2010.

Walle, G., "Non-Destructive Testing with Thermographic Techniques". Technisches Messen TM, vol. 66, No. 9 (1999), p. 312-321.

\* cited by examiner

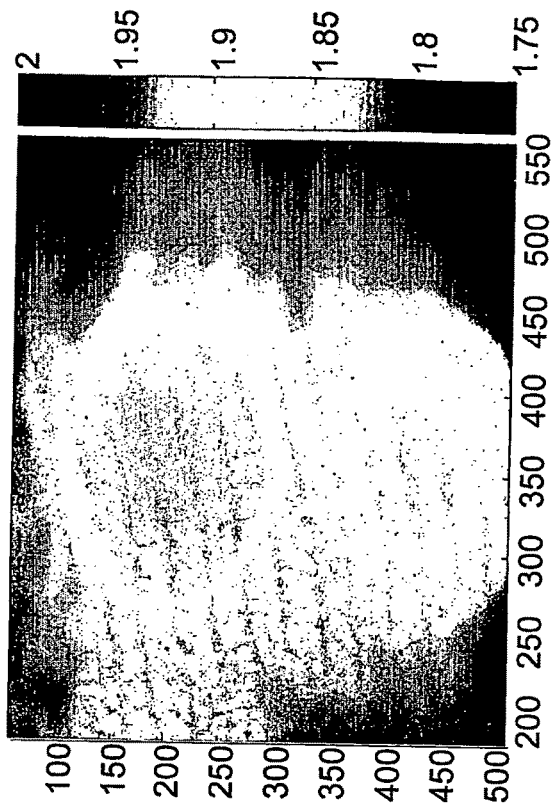
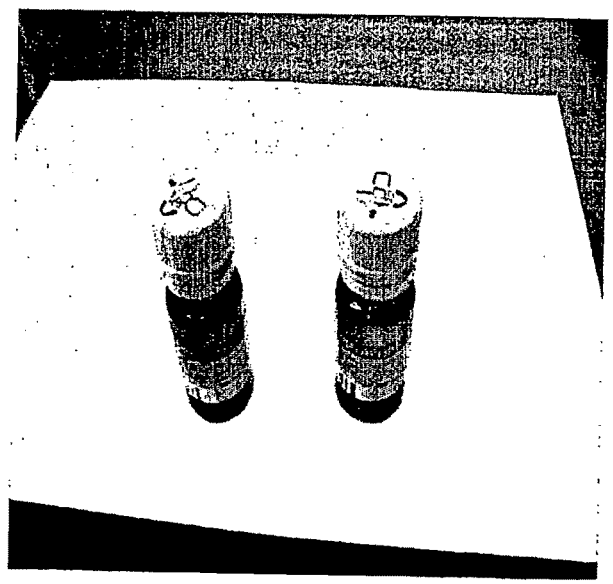
Fig.9b
Fig.9a

THERMOGRAPHY BASED SYSTEM AND METHOD FOR DETECTING COUNTERFEIT DRUGS

FIELD OF THE INVENTION

The present invention relates in general to the field of counterfeit detection systems. In particular, the present invention relates to a system and method for detecting counterfeit of pharmaceutical products. More particularly, the present invention relates to thermography based system and method for detecting counterfeit of pharmaceutical products, which operates in the MWIR or LWIR range.

BACKGROUND OF THE INVENTION

The pharmaceutical industry is a multi-billion dollar international commercial field. Like many industries however, many of the products of the pharmaceutical industry fall prey to counterfeiters who manufacture substandard or fake imitation products, and sell them for a fraction of their real market price. Worldwide, the percentage of drugs that are counterfeit has become high enough to seriously impact the revenue of major pharmaceutical companies. Even more serious is the potential health risks involved for the consumer of counterfeit drugs.

Besides the infringement of intellectual property rights as well as the breaking of other governmental laws, the Federal Drug Administration (FDA) does not yet have an all encompassing solution to the pharmaceutical industry's counterfeit problem.

There have been several attempts by the prior art to overcome the problem of counterfeit drugs, however, each of the prior art solutions has drawbacks associated with it. Some prior art technologies utilize RFID and bar coding to read the package labels to determine the authenticity of the contents contained therein. This, however, does not necessarily provide accurate results since the product itself is not directly analyzed.

The prior art has also developed drug authenticating procedures based on the concept of the spectral signature. Every drug has a unique spectral signature (or, fingerprint) determined by its molecular composition. Infrared (IR) spectroscopy is used to determine whether the molecular composition of the sample product is identical to known spectral signature of the authentic product. IR spectroscopy is the subset of spectroscopy that deals with the Infrared region of the electromagnetic spectrum. Infrared spectroscopy exploits the fact that molecules have specific frequencies at which they rotate or vibrate in relation to discrete energy levels.

U.S. Pat. No. 6,395,538 deals with the fields of bio-manufacturing and infrared spectroscopy, particularly, quality monitoring and control of a biomaterial, for instance in a biologically active pharmaceutical ingredient. Fourier transform infrared spectroscopy is used to monitor the production of a biomolecule and to fingerprint, both qualitatively and quantitatively, the biomolecule at different stages of a biomanufacturing process. U.S. Pat. No. 6,395,538, which as said relates to a spectroscopy based system, is also not concerned with counterfeit drugs on the commercial level, and therefore the system is not concerned with overcoming difficulties such as determining the authenticity of a plurality of pharmaceutical products contained within a sealed package.

U.S. Pat. No. 6,853,447 pertains to the screening and identification of materials such as pharmaceutical or food products being packaged in an automated machine. The invention utilizes an array of imaging spectrometers. The system of U.S. Pat. No. 6,853,447 performs spectroscopy in the near IR and short IR spectra. In contrast to thermography which detects the level of the IR emission from an object and the distribution of the IR emission from the object, spectroscopy checks LR reflection from the product, or more particularly, the spectral distribution of the reflection in the frequency domain The determination of the spectra of U.S. Pat. No. 6,853,447 allows only inspection of the external surface of a product, and cannot relate to the body of the product. Therefore, when applying the spectroscopy of U.S. Pat. No. 6,853,447, each drug has to be inspected individually, outside of its container. This makes it problematic to operate when the pharmaceutical product is in a liquid state. Additionally, many capsules are coated by a thin layer of, for instance, gelatin, which blocks the near IR detector device from determining the authenticity of the drug. Moreover, utilizing such a method on a commercial scale is costly due to the amount of time required for each inspection.

U.S. Pat. No. 6,771,369 relates to the validation and identification of packaged pharmaceuticals in a retail setting. A chemical analysis and validation system preferably utilizes visual (Vis) and near infrared (NIR) spectroscopy to analyze and identify the contents of the filled prescription vial by measuring the chemical signature of the items. Other variations can also be used, for example, various forms of optical spectroscopy, UV-Vis, UV-Vis-NIR, infrared or Raman spectroscopy. The system of U.S. Pat. No. 6,771,369, similar to that of U.S. Pat. No. 6,853,447, produced by the same company, performs detection only in the near and shortwave IR spectra. As described above, operation in these spectra only allow detection of the external surface of a product, therefore, each drug must be inspected individually, outside of the container. On a commercial scale, such a limitation is a severe hindrance to the efficiency of counterfeit checking. Moreover, it is problematic to check a pharmaceutical product in the liquid state. Additionally, as described herein above, many capsules are coated by a thin layer of, for instance, gelatin, which blocks the detector device from determining the authenticity of the drug.

U.S. Pat. No. 7,126,685 describes an optical absorption spectroscopy method comprising providing a container such as a pharmaceutical bottle containing a sample, rotating the container, directing a beam comprising one or more wavelengths consisting of visible wavelengths, infrared wavelengths and ultraviolet wavelengths, and measuring characteristics of the beam after it passes through the container. U.S. Pat. No. 7,126,685 does not deal with detection of counterfeit drugs, let alone on a commercial scale, and therefore does not provide solutions to the above-mentioned counterfeit problems of the industry.

In the prior art, the development of IR technology for the detection of counterfeit drugs has been entirely limited to the field of spectroscopy, particularly near IR. Near IR spectroscopy is restricted in its detection capabilities since it is limited to surface (e.g. drug coating, outer packaging, etc.) reflection. In spectroscopy, the molecular structure of a pharmaceutical product is measured in the frequency domain, and the distinctive curvature is analyzed with corresponding signatures to determine the authenticity of the drug.

Thermography is a type of infrared imaging in which radiation emitted from objects is detected based on the temperature at different locations across the body, and images are produced of that radiation. In passive thermography an image of the emitted radiation is acquired of an object at a steady state temperature. In active thermography, a thermal pulse is applied to the object to change its temperature, and multiple images are acquired during the entire temperature cycle from the moment that the temperature heat pulse is applied until the sample pharmaceutical product reaches the ambient temperature, and over a predetermined time period.

Thermography measures the distribution of the emission from an object, and it operates only in the mid-wavelength IR (MWIR between 3-5.4 micrometers), and the long-wavelength IR (LWIR between 8-14 micrometers). This is in contrast to spectroscopy which relates to the spectral distribution of the reflection from the object mostly in the NIR (near IR) and SWIR (Short Wave IR). It has been found by the inventors that the use of thermography allows inspection deep into the object, i.e., well beyond the surrounding container and the external surface of the object.

While thermal based systems, particularly in the field of thermography, are well exploited in areas such as military/security systems, non destructive testing, and medical imaging, such systems have never been suggested for detecting counterfeit of products, particularly in the pharmaceutical industry.

It is therefore an object of the present invention to provide method and system for determining the authenticity of a pharmaceutical product that overcome the drawbacks associated with the prior art.

It is another object of the present invention to provide method and system for determining the authenticity of a pharmaceutical product by means of thermography, i.e., by means of an IR imaging system which operates in the MWIR or LWIR spectrum.

It is an additional object of the present invention to provide method and system for determining the authenticity of a pharmaceutical product by means of passive or active thermography.

It is still another object of the present invention to provide method and system that can inspect deep into a pharmaceutical product and determine counterfeit.

It is still another object of the present invention to provide method and system that can inspect and determine counterfeit of a pharmaceutical product, even from outside of the product package, and which does not require opening of the package.

It is still another object of the present invention to provide method and system that can inspect and determine counterfeit of plurality of pharmaceutical products that are packaged together, without need for opening the package.

It is still another object of the present invention to provide method and system that can inspect and determine counterfeit of pharmaceutical products from the outside of a multi-layer package.

It is still another object of the present invention to provide method and system that can inspect and determine counterfeit of a liquid pharmaceutical product from the outside of its container.

It is still another object of the present invention to provide method and system that enable a manufacturer of pharmaceutical product to design a hard to counterfeit unique signature for the product, and which can be easily verified.

Additional objects and advantages of the present invention will become apparent as the description proceeds.

SUMMARY OF THE INVENTION

The present invention relates to thermography IR system for determining the authenticity of a pharmaceutical product, the system comprises: (a) a thermography IR apparatus for: (a.1) acquiring at predefined controlled conditions an authenticity signature of an authentic pharmaceutical product, said authenticity signature comprises at least one thermography image of said authentic product, each of said images describes the distribution over said product of the IR radiation in an MWIR or LWIR spectrum as a function of temperature and emissivity; (a.2) storing said acquired authenticity signature in a memory; and (a.3) for a tested pharmaceutical product that corresponds to said authentic product, and whose authenticity is suspected, acquiring at same predefined controlled conditions a test signature, said test signature also comprises at least one thermography image of said tested product, each of said images describes the distribution over said test product of the IR radiation in an MWIR or LWIR spectrum as a function of temperature and emissivity; and (b) a comparison unit for comparing between said authenticity signature and said test signature.

Preferably, said predetermined controlled conditions comprise definition of a temperature variation signal, which in turn comprises a rate of temperature variation that is applied on the product, and a duration of time in which said temperature variation takes place.

Preferably, the corresponding images of each of said authenticity signature and said test signature are acquired at specific times during or following said temperature variation signal.

Preferably, the comparison is made between a selected single image from each of said authentic and test signatures.

Preferably, the comparison is performed between corresponding two images from said authentic and test signatures, wherein each of said images in turn reflects a mathematical operation which is performed on corresponding single or plurality of images that are acquired at specific times during or following said temperature variation signal.

Preferably, said predetermined controlled conditions further comprise definition of a type of heat source for effecting said temperature variation.

Preferably, said predetermined controlled conditions further comprise definition a profile of said temperature variation.

Preferably, said predetermined controlled conditions further comprise definition a distance from the heat or cooling source.

Preferably, said predetermined controlled conditions further comprise definition of signature images capturing in the LWIR, MWIR, or both.

Preferably, said predetermined controlled conditions further comprise definition of one or more filters, each filter limits the image capturing to spectrum range.

In one embodiment, said pharmaceutical product is a solid medicine.

In another embodiment, said pharmaceutical product is a liquid medicine.

Preferably, each of said authentic and corresponding test signatures comprises one or more thermography images of the product package.

Preferably, said authentic and corresponding test signatures of the product are acquired while the package contains or does not contain the pharmaceutical product itself.

In one embodiment, said solid pharmaceutical product are pills that are packaged within a paper carton package.

In another embodiment, said solid pharmaceutical product are pills that are packaged within an aluminum or plastic package.

In another embodiment, said solid pharmaceutical product are pills that are packaged within one or more aluminum or plastic packages, that are in turn contained within a paper carton package, and wherein said conditions include acquiring of the images from outside of said paper carton package.

In still another embodiment, the liquid pharmaceutical product is contained within a container, and wherein said conditions include acquiring of images from outside of said container package.

Preferably, the memory comprises a remote or local database, wherein the database contains plurality of authenticity signatures for one or more pharmaceutical products.

In one embodiment, the memory comprises a remote database, and wherein the comparison is performed remotely, at the location of said remote database.

In an embodiment of the invention, the comparing unit comprises image processing means, for performing automatic comparison between images, and wherein the authenticity is decided upon finding similarity above a predefined threshold.

Preferably, the comparing unit comprises a display for displaying one besides the other of authentic and corresponding test images, for enabling visual comparison by an operator.

Preferably, the system further comprises a signal generator, for producing said temperature variation signal.

According to various embodiments of the invention, said temperature variation is performed by means of one or more of:
an oven;
a microwave;
an IR lamp;
a laser beam.
Cooled by gas expansion
Thermal electric cooler
Ultrasonic waves.

According to various embodiments of the invention said temperature variation is performed in a form of one or more of:
a delta function;
a step function;
a rectangular function;
a saw tooth function; and,
a periodic function.

In an embodiment of the invention, said thermography IR apparatus comprises: (a) a thermography 2D focal plane array for detecting IR radiant energy in the MWIR and LWIR ranges; (b) optical components for focusing the radiation on the focal plane array; and, (c) a controller for operating said focal plane array, and for converting the analog output of said array to a digital high resolution image.

In an embodiment of the invention, the authentic and test signatures also relate to images that reflect 2D radiation from the pharmaceutical product in one or more of the ranges of 5.4-8 μm and 14-20 μm.

In an embodiment of the invention, said conditions comprise use of one or more IR polarizers.

In an embodiment of the invention, the authentic pharmaceutical product is intentionally engineered to introduce a distinguished authentic signature when operating in conjunction with the system of the invention.

In an embodiment of the invention, said engineering of the authentic product includes one or more coating or edible materials.

In an embodiment of the invention, said edible materials are air bubbles that are added at specific pattern to the product.

In still another embodiment, the authenticity verification is expanded to also include verification of meeting storage conditions of the pharmaceutical product during its life, wherein the product is coated by an edible thin film which changes its emmisivity and morphology when exposed to destructive storage conditions, and by this changes also its authenticity signature.

In still an embodiment of the invention, the pharmaceutical product is contained within a package, which in turn comprises internal heating element, and wherein said temperature variation signal is provided to said element in order to effect said temperature variation.

In still another embodiment of the invention, the thermography apparatus is a 1 pixel measurement apparatus.

BRIEF DESCRIPTION OF THE FIGURES

In the drawings:

FIG. 9a shows an image of authentic and counterfeit filled liquid Optalgin containers respectively, as obtained by a CCD (VIS) camera;

FIG. 9b shows the same containers of FIG. 9a respectively, as seen by a cooled InSb apparatus of the invention;

DETAILED DESCRIPTION OF THE PREFERRED EMBODIMENTS

Figure 1:
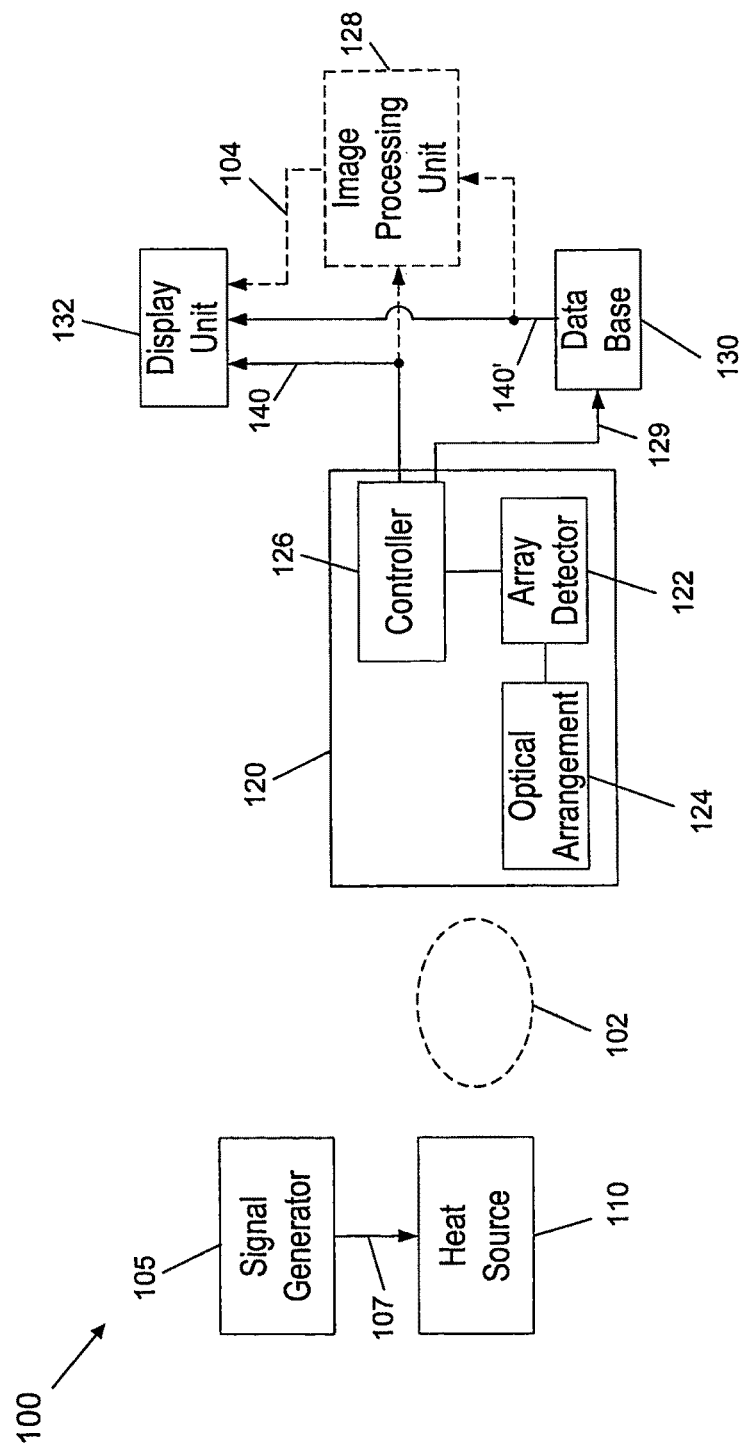
FIG. 1 illustrates a block diagram schematically showing the components of a first embodiment of the system of the present invention.

There are currently no complete solutions to the problems associated with counterfeit drugs. The present invention provides a novel method and system for determining the authenticity of a pharmaceutical product, using a thermography based system. The system can determine counterfeit even without removing the product from its cover, package, or container.

The term, "pharmaceutical product" as used herein refers to any form of drug, for example, a tablet, capsule or solution, and is used herein interchangeably with the term, "drug".

According an embodiment of the present invention, a thermography signature of a sample of each of a plurality of authentic pharmaceutical drug products is initially collected and stored in a database. Said initially collected signature will be referred to hereinafter also as the "authentic signature" of the drug. The thermography signature is a thermography (i.e., in the LWIR or MWIR range) two dimensional view of the drug product, which is collected at a controlled, specific condition of the product. Such a specific condition may be, for example, the 2D response of the drug product over time to a heating (or cooling) signal, the response after a specific predetermined time after the initiation of the signal, etc. The form of said heating or cooling signal is predefined, but may vary (just for example, it may be a square pulse; a saw tooth signal, etc.). Furthermore, and as will be elaborated, the response may be limited to a specific wavelength within the LWIR or MWIR ranges, it may use polarization, etc. In any case, it has been found by the inventors that such a response is very unique to the composition and structure of the drug product, and is very hard to imitate.

As mentioned, the MWIR and LWIR ranges are conventionally referred to in the art to the ranges between 3-5.4 micrometers and between 8-14 micrometers respectively. Said definitions are originated from the fact that the atmosphere generally absorbs IR between said ranges (i.e., between 5.4 to 8 micrometers). However, the present invention may utilize also said latter rage of 5.4 to 8 micrometers, and even the range of VLWIR of 14-20 micrometers and there are various detectors that are sensitive also in said latter ranges. Therefore, the use of MWIR and LWIR throughout this application should not be viewed as limiting its scope not to include the range of 5.4 to 8 micrometers and/or 14-20 micrometer.

According to the present invention, the signature of any given drug product in the market, whose authenticity is suspected, is compared to said authentic signature, for verification as to whether it is authentic or not. The comparison is made essentially in the same condition as was used upon collection of said authentic signature.

For example, the signature may be displayed as one or a series of visual images of the drug, and may be quantified by a value for comparison with a corresponding sample drug, as described herein below. Since it is assumed that a counterfeit drug comprises a different molecular composition (and sometimes structure) than that of an authentic drug, the MWIR or LWIR emission, e.g. as a function of time (i.e.: the signature) of the authentic drug is different than that of a counterfeit drug.

The inventors of the present invention have found that the use of a thermography system for detection of counterfeit products in the MWIR and LWIR spectra, particularly, but not limitatively, after the providing into it a heating or cooling signal (hereinafter, for the sake of brevity both terms will be briefly referred to as a "heating signal"), has considerable advantages over prior art detection systems of counterfeit drugs, which utilize spectroscopic devices and methods. For instance, as noted herein above, prior art technologies use detection systems in the near-wavelength infrared (NIR) spectrum, which are based on reflections from the product, and therefore enable inspection of only the external surface of the drug. Said spectroscopic based prior art systems generally have difficulties in passing through the drug container, coverage, or package (hereinafter, all said terms will be referred to as "packages"), and in any case it requires opening of the package. On the other hand, the thermography MWIR or LWIR detection system of the present invention allows detection of the internal molecular changes of the drug, which bypasses the coating layer of the package that may be present on the surface of a capsule (or on any other form of the drug). In other words, the MWIR and LWIR detection system of the invention passes through the package of the drug and therefore does not require opening of it. This allows the operator of the system to determine the authenticity of the drug even when it is contained within an entire container, or even within an entire crate or carton, in a single procedure, thereby significantly improving the efficiency of the detection process on the commercial scale. In addition, by allowing the pharmaceutical product to remain within the container, the process for detecting the authenticity of a drug in the liquid state is much more practical than that afforded by a procedure performed utilizing the spectroscopic based system of the prior art.

The use of a thermography system allows the detected signature to be displayed in a form of an image, in which the variation in temperature and radiated emission are clearly shown. This allows a greater ability to distinguish between drugs on a visual scale.

FIG. 1 shows in block diagram form the general structure of a first embodiment of the thermography IR system 100 of the present invention. System 100 comprises a heat source 110 for heating (or cooling) a sample pharmaceutical product 102 to a modified temperature, thereby to change its IR emission in the MWIR or LWIR ranges. System 100 further comprises a thermography apparatus 120 for detecting the emitted radiation from pharmaceutical product 102. Said detection may be continuous, or it may be carried out some predefined period from the moment that the temperature heat pulse has been applied. Said detection conditions should conform as much as possible the conditions in which the authentic signatures that are saved in data base 130 have been collected. Thermography apparatus 120 comprises one or more IR array detectors 122 (commonly referred to in the art also as "focal plane arrays") for sensing IR radiant energy in the MWIR and LWIR ranges, and converting them into an image. Such arrays are well known in the art, and are used, for example, in night vision thermal systems. Optical arrangement 124 focuses the radiation onto the two dimensional array 122. Said optical arrangement may include one or more lenses, filters and/or polarizers. Controller 126 operates the array 122. The Controller also receives an analog signal from the detector array 122 which describes the thermography emission from drug product 102. Controller 126 also converts the signal from the array to a digital high resolution 2D present product image 140. The 2D image 140 of the radiant emission from the pharmaceutical product 102, is displayed on display unit 132. As said, database 130 stores plurality of authentic signatures of many authentic drug products. Said stored signatures can generally be shown as images. In one embodiment of the invention, controller 126 extracts 129 the authentic signature 140' of drug 102 from database 130, as previously collected from an authentic drug, and displays the same side by side with present image 140, for visual inspection. It should be noted that on display unit 132 the signature levels of the IR emission are displayed in various colors, to emphasize said varying spatial emission from the product. As noted above, it has been found. that there is a very clear visual distinction between the image 140 of an authentic drug, and of a counterfeit drug in all common drugs that have been tested by the inventors. It should be mentioned again, that the present signature is obtained in a same controlled condition as of the authentic signature. In any case, the authentic signatures within data base 130, and the conditions in which they are collected, can be easily defined to reflect and emphasize such distinction. Some of the options for varying such conditions will be elaborated hereinafter. Optionally, instead of the visual inspection and comparison of the images on screen 132, the comparison may be made automatically by image processing unit 128. Image processing unit 128 determines the correlation factor between the present signature and the stored authentic signature from database 130 and evaluates whether the correlation factor is above a predefined threshold. Following this evaluation, image processing unit 128 establishes a conclusion regarding as to whether the sample 102 is authentic or counterfeit, and said conclusion 104 may be displayed on display unit 132, or notified to the user in any other conventional form.

In another alternative, the tested (suspected) drug product may be compared to a reference drug product which is known to be authentic instead of a pre stored signature within the data base. This comparison, in a similar manner to the process as described before, can be performed either by visual inspection or automatically by applying image processing algorithm.

The database 130 may be located at various locations. In one embodiment database 130 is located within the testing apparatus. In another embodiment, data base 130 is maintained in a secured manner within a secured site, and relevant authentic signatures are extracted from there by the testing apparatus via the Internet (or any other communication, such as cellular technology). In still another embodiment, data base 130 is maintained in a secured manner within a secured site, the image 140 is conveyed via the Internet to said secured site, and the comparison is performed within said secured site, which in turn conveys into the testing apparatus a yes/no result regarding the authenticity of the product. As said, in still another alternative, the comparison may be made to an image which is locally extracted from a physical ("master") product which is known for sure to be authentic.

Heat source 110 is preferably controlled by a signal generator 105. Heat source 110, together with signal generator 105, imitate the same condition in which the authentic signature of drug 102 has been collected. Heat source 110 may be, for instance, an oven, a microwave, an IR lamp, a laser beam, etc., for heating (or cooling, for example by means of gas expansion), an individual drug (e.g. a capsule), or an entire container thereof. The heat signal 107 from generator 105 may be a delta function, a step function, a rectangular function, a periodic function, a saw tooth function, or any other designated function. It is important to note that the response of the drug to the heat differs depending on the type heat applied to the drug (e.g., oven, microwave, etc.), as well as on the type of heat signal as provided from generator 105. Thus, whenever necessary, in order to obtain a more comprehensive characterization of the sample drug 102, more than one combination of heat source and heat signal 107 may be used. Moreover, plurality of signatures that reflect the change of emission from the drug over time, or responsive to polarization or filtering may also be used. Of course, in this case, the database requires the storing of the plurality of authentic signatures for comparison, as a function the signal form, of time, wavelength, polarization, heat source type, etc.

In one embodiment, IR thermography apparatus 120 may comprise both a cooled detector and an uncooled detector. A cooled detector is capable of detecting Infra Red radiant energy in the range of MWIR (3 µm-5.4 µm). The detector array comprises, for example, 320×256 individual elements in the size of about 30 µm each pixel, or alternatively, 640× 512 individual elements in the size of about 15 µm pitch. In that case, the array may be made of InSb (Indium Antimonide) or MCT (Mercury Cadmium Telluride), and operated at cryogenic temperature. Furthermore, the detector array may be connected to the focal plane processor (FPP) array (not shown in the figure) by means of Indium bumps, and may be illuminated from the back side. An uncooled detector is an electro optical assembly which converts Infra Red radiant energy in the range of LWIR (8 µm-14 µm). The uncooled detector is built of a detector array which is housed in an evacuated Dewar. The uncooled detector array comprises, for example, 320×256 individual elements in the size of 20-30 µm each pixel, or alternatively, 640×512 individual elements in the size of 20-30 µm pitch. The array may be fabricated from VOx (Vanadium Oxide) or Amorphous Silicon, and is operated at around room temperature.

It is understood that alternative cooled and uncooled IR detectors having different capabilities and structures may be used for the purpose of the present invention. For instance, an LWIR (8 µm-12 µm) array detector may alternatively be cooled from MCT or a QWIP (Quantum Well Infrared Photodetector) sensor.

Although not necessarily required, in one embodiment, Filter/optics arrangement may comprise a set of filters, for example, in a form of a filter wheel (See FIG. 2), well known in the art. The wheel may include a set of narrow band filters, preferably from the MWIR to the LWIR, and/or IR polarizers. Alternatively, any optical device that can change the spectral transmission properties at high frequency may be utilized.

Figure 2:
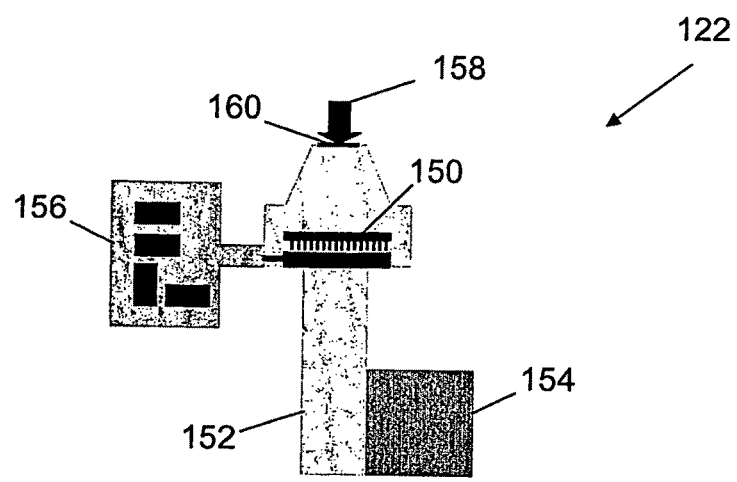
FIG. 2 illustrates a schematic diagram of the cooled detector utilized in the first embodiment of the present invention.

FIG. 2 shows the assembly of a cooled thermography array detector 122 in a schematic form. Array detector 122 comprises a focal plane array 150 and an electronic interface board 156. A vacuum chamber 152 is shown joined with a cooler 154. In the alternative case when an uncooled detector is used, the assembly does not comprise a cooler 154. However, in order to maintain the focal plane array at a steady temperature a thermo-electric cooler (TEC) may be provided instead. When an object emits IR radiation as indicated by arrow 158 it is filtered by filter 160 and impinged on focal plane array 150 in the desired wavelength.

Thus, in the above embodiment for performing the authenticity detection procedure of the present invention, active thermography is performed. In this case, a sample drug is obtained and heated by a heat source 110, which is in turn controlled by a signal generator 105 (which issues, for example, a step function, delta, rectangle, periodic etc.). During at least a portion of the heating and/or the relaxation period (i.e., the cooling of the product), the emitted IR radiation is sampled at least once by the thermography IR system, in a manner which conforms the condition as maintained when the authentic signature was collected. For example, a drug product is heated by a heat pulse for a predetermined period of time until the original temperature of the product drug is raised a predetermined amount to a modified temperature. The pharmaceutical product is then allowed to cool back to its original temperature. During at least a portion of the heating period and/or cooling period, the thermography apparatus of the present invention samples the emitted radiation to determine the signature of the sample drug. The signature of the drug, as presently obtained, is compared, either visually on the display, or automatically by means of a signal processing unit, with the corresponding authentic signature of the drug as previously obtained and stored within database 130.

As said, the emitted radiation response as a function of time (i.e, either a continuous varying response or the radiation after a specific period from the moment of initiating the heating) of the sample drug and is compared to the signature of the corresponding authentic version of the sample drug. If the signature of the authentic version of the drug is identical, or at least highly correlated above the predetermined threshold to the sample drug, then the sample is considered to be authentic. If, however, the signature of the authentic drug is not identical or highly correlated above said predetermined threshold to the sample drug, then the sample is considered to be counterfeit. If the sample drug is counterfeit, necessary actions may be taken, depending on the various circumstances in which the counterfeit drug was discovered.

As previously said, in an alternative aspect the sample drug is cooled by a thermal pulse generator (e.g. a quick cooling method such as gas expansion) for a predetermined amount of time, until it reaches a predetermined modified temperature. The response is acquired during the entire pulse, during a specific time after the initiation of the pulse, even at some time after the end of the pulse. In a similar manner to as described above, also in the case of cooling, the authentic signature, as well as the signature from the presently tested product are obtained in exact same controlled conditions (i.e., same pulse, same cooling or heating temperature, same period, etc.).

In one alternative, in order to ensure accurate controlled conditions, the drug product may be put on an extended black body (such an extended black body is known in the art, and is manufactured, for example, by CI Inc.).

In another alternative, the entire testing process is performed within a temperature stabilized and controlled chamber which ensures uniform ambient temperature conditions.

In the case wherein the signature of the authentic version of the sample drug has not been previously recorded and stored in the database, the signature of the sample drug is acquired as described herein above, and stored in a secondary database of the system of the present invention until the authentic version of the sample drug is acquired, at which time the signature of the sample drug is compared thereto.

According to an alternative aspect of the present invention, passive thermography is performed, wherein the sample remains at ambient temperature, and is not heated or cooled. According to this embodiment, the IR detector system detects only the steady state radiant emission in the MWIR or LWIR spectral wavelength, and not as a function of time. Thus, the database in that case contains suitable temperature signatures of authentic drugs in the MWIR and/or LWIR spectra for a specific ambient temperature.

In another alternative, the entire testing process may be done inside a temperature stabilized and controlled chamber which ensures uniform ambient temperature conditions within the chamber.

In still another embodiment, the product package itself (for example, the aluminum package of the pills) may include one or more internal heating elements. The one or more heating elements in that case are activated by providing to them a corresponding external electric signal, that in turn causes the pharmaceutical product to heat.

According to the present invention, additional secret identifying information may be added by the manufacturer to the authentic drug during the manufacturing process in order to further distinguish it from a counterfeit drug. For instance, an internal barcode in the form of air bubbles may be included by the manufacturer within the drug. There are many other possible ways by which additives may be included within the drug, which affect response in the MWIR or LWIR, but not the medical effectiveness of the drug. While such an addition to the drug has no significant effect, if any, on the medical effectiveness of the drug (and therefore, will not require additional regulatory approval by the FDA), it may significantly affect the authentic signature of the drug to a rate which is hard to imitate, or which form a distinguishable signature from a signature of a drug which is known to be counterfeit. It should be noted that the drug manufacturer may also include such additive on the drug package. For example, the drug manufacturer may include a portion on the drug or package that has a very high emmisivity, heat capacity, etc.

In still another aspect of the invention, the present invention enables the determining as to whether the drug has been exposed during its life to improper heat conditions. In that case, the drug is coated by an edible thin layer that changes its physical properties when exposed to a temperature above some predefined allowed limits Just for example, the drug may be coated by a thin chocolate layer, and the authentic signature of the drug includes such layer. Later on, if the drug has been exposed to some temperature above a room temperature, this coating melts, and it affects also the signature of the drug (MWIR or LWIR, active or passive radiation, as is the case) as obtained by the apparatus of the present invention. In such a manner the apparatus of the present invention can detect not only counterfeit, but also it can ensure quality of the drug that may suffer improper storage conditions throughout its life. Moreover, in a similar manner the apparatus of the invention can also ensure the quality of a drug, and detect a drug has been mistakenly manufactured while lacking some of its ingredients. Such a lack of ingredient generally involves deviation from the authentic signature in terms of MWIR or LWIR 2D emission. Therefore, for the sake of brevity, the quality assurance as described herein will not be distinguished throughout this application from a conventional counterfeit. In other words, the term "counterfeit" of drug relates to any deviation of the authentic drug ingredients, no matter what is the reason that has caused this deviation.

In still another embodiment of the invention, although the present invention has been described herein with reference to detecting counterfeit drugs, the application of the method and system described herein may be equally be useful for the identification of other counterfeit products such as currency, diamonds, food products, or other products in which a deviation from their authentic "ingredient" materials result in a change in time of their 2D (thermography) LWIR or MWIR emission, for example, after being subjected to some predetermined controlled temperature change. Therefore, in one specific embodiment of the invention, the term "drug" in this application may be expanded to include said other types of products (although they are actually not drugs).

The thermography apparatus of the present invention can detect a counterfeit drug by applying one or more of the following techniques:

1. Predetermining a rate of temperature variation (i.e., minimum to maximum temperature or vice versa) that will be applied to the sample (i.e., to the "master" authentic drug, and to the drug in question);
2. The type of heat source that will be used to effect said temperature change, for example, a typical oven, a microwave based oven, a laser based heating source, a refrigerator, a thereto electric cooler, etc.;
3. The profile of the temperature variation signal, i.e., a spike, a saw tooth signal, a step signal, a cyclic signal, etc.;
4. The distance from the heat (cooling) source;
5. The type of detector, i.e., a cooled (MWIR) detector, or a non-cooled (LWIR detector);
6. The option of applying averaging of the response from the sample at two times, e.g., at predetermined times $T_1$ and $T_2$. It should be noted that use of other types of mathematical operations is also possible, either in the time domain or in the spatial domain. Analysis in the time domain means analysis on several frames that are obtained during some times, for example, averaging of 10 sequential images. Analysis in the spatial domain means the application of some image processing algorithm on a single image, for example, in order to emphasis the edges of the authentic and/or tested images. Specific examples for operations in the time domain are averaging over time of frame images, STD (Standard Deviation) of frame images over time, Fourier transform over time, low pass filter in the time domain, or high pass filter in the time domain. Specific examples for operations in the spatial domain are FFT (Fast Fourier Transform), Wavelet Transform, Discrete Fourier Transform (DFT), Discrete Cosine Transform (DCT), low pass, or high pass. These are only examples, and other mathematical operation in the spatial or time domain may be applied.
7. The option of using one or more filters in order to limit the response to a specific optical range.
8. The option of comparing between the signatures of the authentic and the suspected external packages (aluminum or paper carton or plastic packages) of the pills, or the internal aluminum packages of the pills;
9. As mentioned, the authenticity verification by the system of the invention includes predefined conditions that are applied to the product when obtaining the authenticity and test signatures. These conditions, although predefined, are very flexible. Therefore, if for some reason it is found that the apparatus of the invention cannot clearly distinguish between a specific authentic and counterfeit drug when one specific condition is applied, the predefined condition can be easily modified in order to find a more suitable condition. The fact that the various parameters that form the possible conditions can vary within very large ranges, there is almost no doubt that a suitable condition can be found for each and every pharmaceutical product in the market, that will result in a distinguishable authenticity signature for that product.

All the above options may be used, while defining the conditions for obtaining the drug signature. It should be noted that the conditions may change from one drug to another, in order to find a condition which provides a distinguishable result. Such conditions may be decided specifically for each drug upon having known counterfeit drugs, in order to find a condition that best distinguishes the authentic drug from said given drug product which is known to be counterfeit. Therefore, various conditions may be applied for various drugs or type of drugs. Furthermore, the apparatus may operate in one of the following modes:

1. An automatic mode in which the evaluation is performed by means of image processing which compares (correlates) between the images of the authentic and the suspected drug;
2. Image processing as in item 1, while a specific operation is applied to the image, such as high pass, low pass, FFT, DFT, DCT, etc.;
3. Manual mode in which the operator of the apparatus visually compares between the two images. As will be demonstrated by the following example, operation in such manual mode provides very good results in many real typical counterfeit cases;
4. In one option, the apparatus may only collect a signature from the suspected drug, and conveys it to a secured site (who maintains a bank of signature) for comparison. In that case, the comparison is performed in the secured site. Following said comparison, the secured site returns the yes/no result to the apparatus;
5. In still another option, the apparatus comprises within it a local database of signatures for various drug types.
6. In another option, the comparison is made locally between a signature as obtained from a suspected drug and a signature as obtained at same time from a drug which is physically available to the operator and is known to the operator to be absolutely authentic (a "reference drug"). At the time when verification is necessary, the apparatus first extracts in site the authentic signature from the reference drug, then it extracts a signature from the tested drug, and then it performs comparison between said two signatures and provides a final conclusion.

In still another embodiment of the invention, the MWIR or LWIR array detector 122 is a single pixel "array" (although the term "array" generally refers to plurality of sensors and not to a case when only one sensor is used, for the sake of brevity the present invention uses the term "array" also when said array includes only one sensor, i.e., pixel). More particularly, the array includes only one IR sensor. There three alternative options for operating with said one pixel array, as follows:

a. While obtaining the authentic signature from the drug, the drug product (such as a pill) 102 is positioned at a predetermined fix position and orientation in relation to the one pixel array, and the signature (i.e., radiation from the drug) is obtained by said one pixel array with respect to a predefined one point over the external surface of drug product 102. In that case, the optics 124 directs the one pixel array toward said predefined point. While obtaining the test signature from the drug product, the drug in question is positioned exactly in the same position and orientation as defined for the authentic drug, such that the comparison is made with respect to a same point respectively in said two, authentic and tested drugs.

b. While obtaining the authentic signature from the drug, the drug product (such as a pill) is positioned at a predetermined fix position and orientation in relation to the one pixel array, and the signature (i.e., radiation from the drug) is obtained by said one pixel array with respect to the whole drug. In that case, the optics 124 images the whole drug on the one pixel array such that radiation from the whole drug product is measured. While obtaining the test signature from the tested drug product, the drug in question is positioned exactly at the same position and orientation as defined for the authentic drug, such that the comparison is made with respect to a same orientation in said two, authentic and tested drugs.

c. The third alternative option is the same as the first option described above. However, the optics is movable such that it "scans" the drug product in such a manner that each time another point on the external surface of the drug product 102 is measured.

It should be noted that said one pixel array embodiment (particularly its first two alternatives) is generally more simple and of lower cost, so it more suitable for use by the end user of the drug, for example in its home.

It should also be noted that the system of the invention may operate in principle in two modes of operations, which are referred to herein as "active" and "passive". In the passive mode, the authenticity and test signatures are obtained in the ambient temperature, without the application of a heating or cooling signal. Generally, in the passive mode the IR radiation is a function of (a) the emissivity of the object, (b) the selected wave length band (MWIR, or LWIR etc), (c) the object temperature (Plank equation), and (d.) the ambient temperature. The operation of the thermography system in the passive mode therefore reveals mostly properties of the surface of the object, not of its full internal structure. In the active mode, the authenticity and test signatures are obtained following or during the application to the object of a heating or cooling signal. In that case, the IR radiation from the product is a function of: (a) the operating wave length band. (MWIR or LWIR, etc), (b) the product temperature (Plank equation), (c) the ambient temperature, (d) the emissivity of the object, (e) the thermal conductivity of the object, (f) the object heat capacity, (g) the object thermal convection, and (g) the absorption of the thermal pulse due to object molecular structure. Therefore, the use of the invention in the active mode is preferable, as it reveals various properties of the object that are not revealed while operating in the passive mode. A full imitation of all said properties in the counterfeit product that are all affect the results of the active mode operation of the system of the invention, is essentially impossible.

EXAMPLE 1

Figure 3:
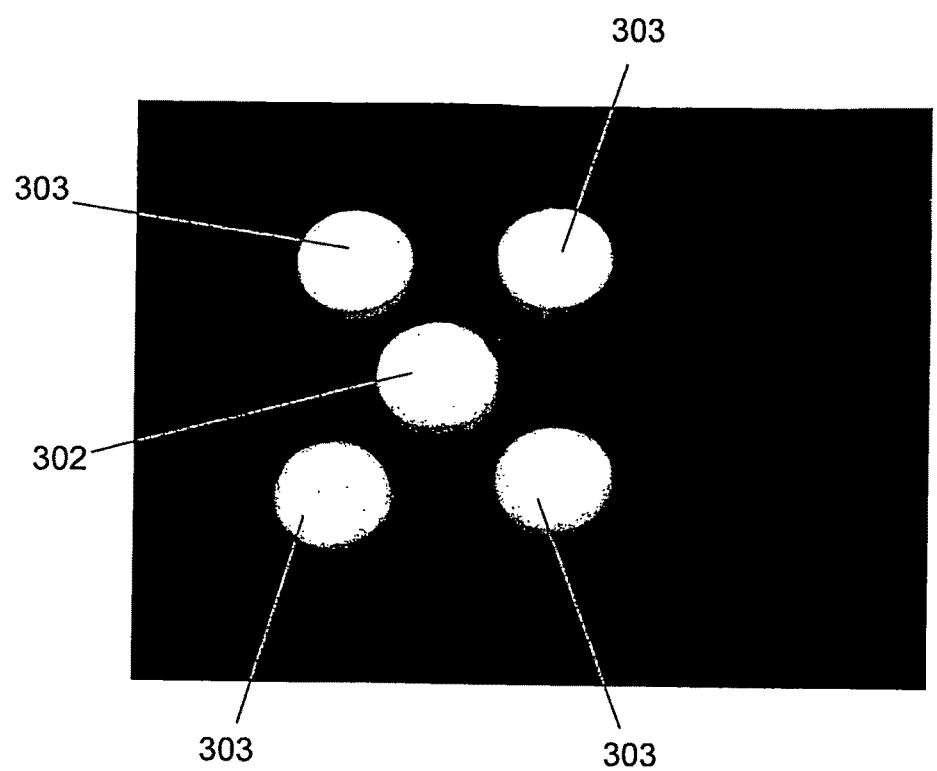
FIG. 3 shows an image of five pharmaceutical tablets, four authentic and one counterfeit, as acquired by a standard CCD camera.

Five drug samples (tablets) were obtained for detection via active thermography using the system of the present invention. Four tablets were authentic and one tablet was counterfeit. FIG. 3 shows an image of the five samples acquired from a standard CCD camera. As can be seen, all five samples are essentially identical in appearance (color, shape, dimensions) to the human eye, as well as in weight. The middle tablet 302 is counterfeit, whereas the surrounding tablets 303 are authentic.

The tablets were placed on an open surface calibrated at 40° C. A pulse was applied to cool the tablets from 40° C. to 20° C. The MWIR emission from each tablet was detected using the system of the present invention during the cooling process.

Figure 5:
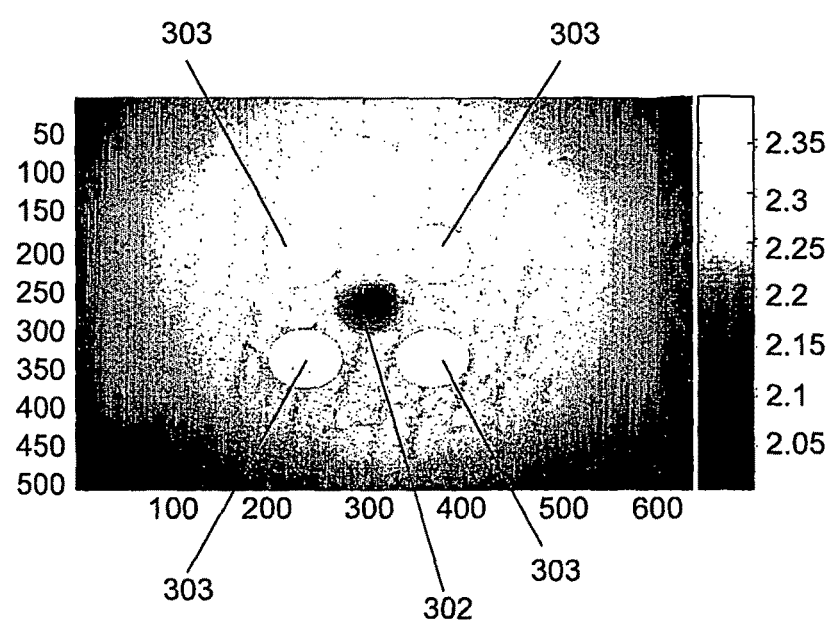
FIG. 5 shows a two dimensional thermography image of the tablets of FIG. 3 as obtained by the apparatus of the invention at t=10 seconds, following the application of the cooling pulse.
Figure 6:
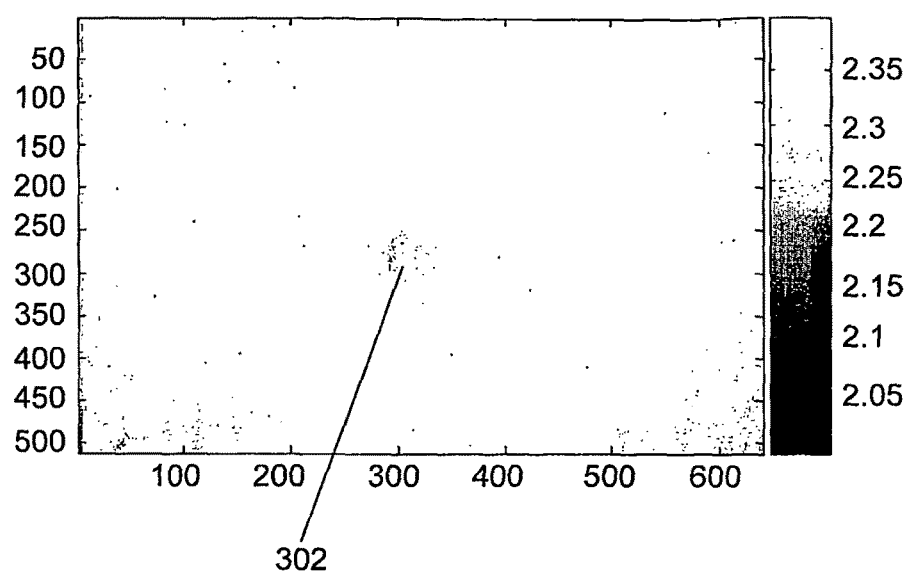
FIG. 6 shows a two dimensional thermography image of the tablets of FIG. 3 as obtained by the apparatus of the invention at t=15 seconds, following the application of the cooling pulse.

In FIGS. 5-7, the thermography image of the tablets is shown using a detector array comprising 640×512 individual elements. It should be noted that the images in the experiment, as performed, included a display in a colored scale, in which the coldest temperature was indicated as blue, while the hottest temperature was shown as red. The color in this scale was varied between these two extremes for displaying other temperatures accordingly. Therefore, in this experiment the determination of a counterfeit drug was even easier and more distinguishable than in the black and white images as provided in this application. For this reason, the present invention encourages using such a colored scale for displaying varied MWIR or LWIR temperature emissions.

Figure 4:
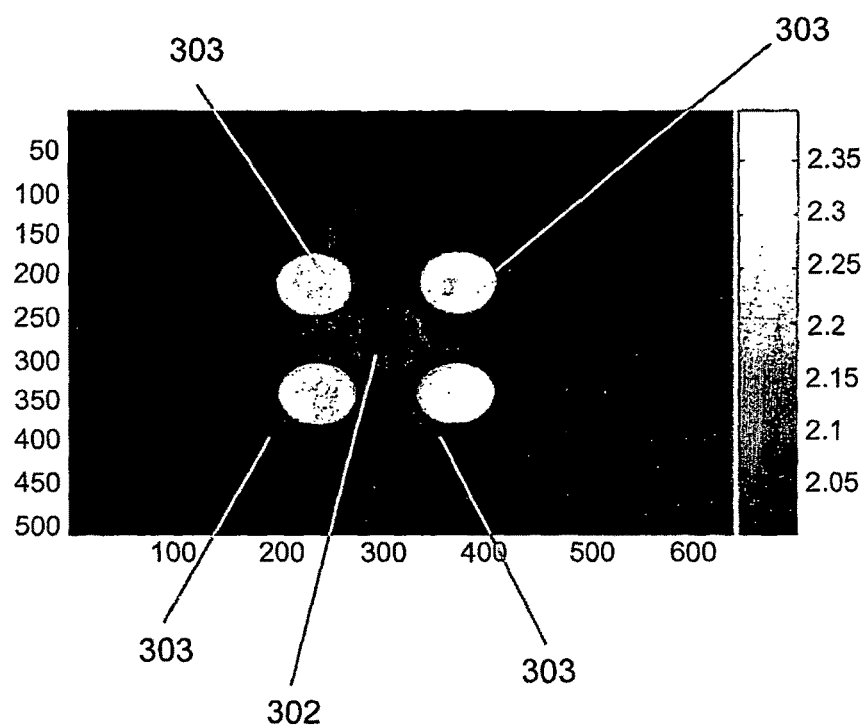
FIG. 4 shows a two dimensional thermography image of the tablets of FIG. 3 as obtained by the apparatus of the invention at t=1 second, following the application of the cooling pulse.

FIG. 4 shows a two dimensional thermography image of the tablets 302, 303 at t=1 second, following the application of the cooling pulse. Thermography images of the tablets 302, 303 were then acquired at 10 seconds (FIGS. 5) and 15 seconds (FIG. 6) as further cooling took place. FIGS. 5-7 thus show the change in the thermography emission over time and temperature change from 40° C. to 20° C.

The thermography image of counterfeit drug 302 is clearly different from that of authentic drugs 303. The thermography images of the figures show authentic drugs 303 progressively becoming lighter in appearance until they are nearly undetectable by the human eye (FIG. 6) in front of the background as shown. Counterfeit drug 302, in comparison to FIG. 4 which has been taken after the first second, became darker in FIG. 5, and then became slightly lighter by the fifteenth second image of FIG. 6.

EXAMPLE 2

A feasibility test was performed using an InSb cooled detector. The feasibility test compared between an authentic Cialis and a counterfeit Cialis, as provided by the Pharmaceutical Crime Unit, the Ministry of Health, the State of Israel.

The lab prototype consisted of:
1. A cooled detector in the MWIR region (3 μm-5.4 μm);
2. Optics;
3. Electronic circuitry for acquiring a 2D digital spatial image from the detector outputs; and
4. An extended black body for applying a heating signal.

Figure 7A:
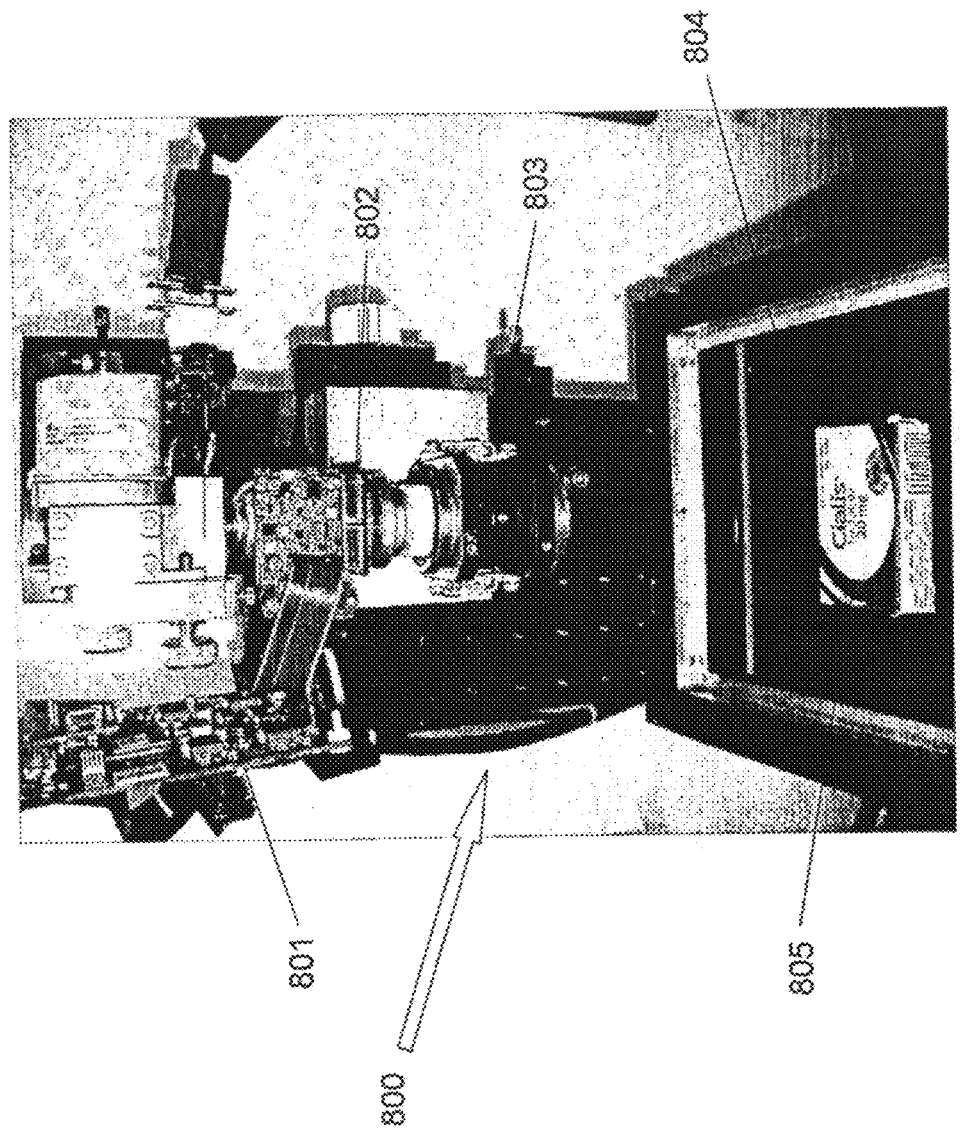
FIG. 7a shows an InSb cooled prototype apparatus by which the invention was tested.

The prototype apparatus is shown in FIG. 7a. The apparatus comprises electronics 801, focal plane array 802 in the MWIR range, Optics 803, and a black body 804 manufactured by CI Inc. A Cialis package 805 is shown placed on said black body 804.

Several tests were performed. During the tests, various samples were placed on black body 804. In each of said tests, the black body was initially set to 30° C. After stabilizing the temperature of the black body at 30° C., its temperature was reduced to 15° C., while recording every 1 second the emission of the drug during the entire temperature change. The sequence of 10 images that were obtained was averaged to provide a single image for each test. The two authentic and counterfeit images were compared.

Figure 7B:
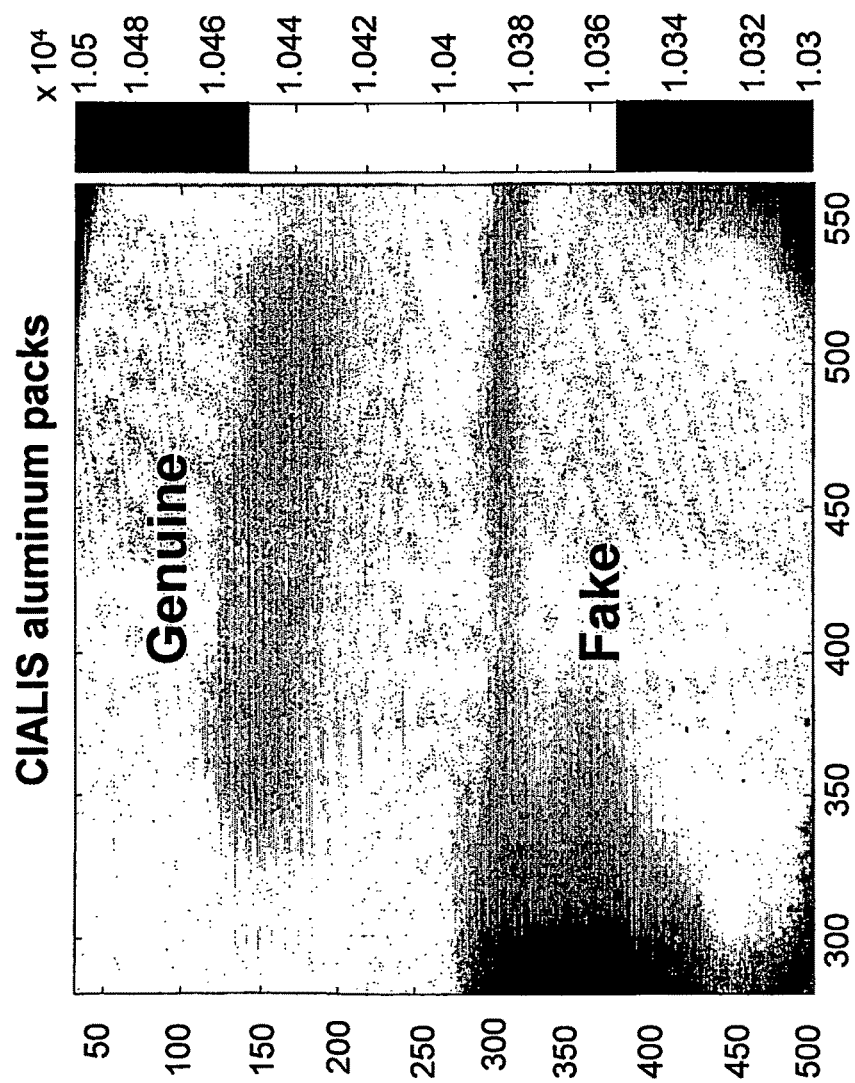
FIG. 7b shows a comparison as obtained by the apparatus of FIG. 7a, between two empty aluminum packages of authentic and counterfeit Cialis pills.

FIG. 7b shows a comparison as obtained by the apparatus, between two empty aluminum packages of authentic and counterfeit Cialis pills. It can be seen that the images are very easily visually distinguishable.

Figure 7C:
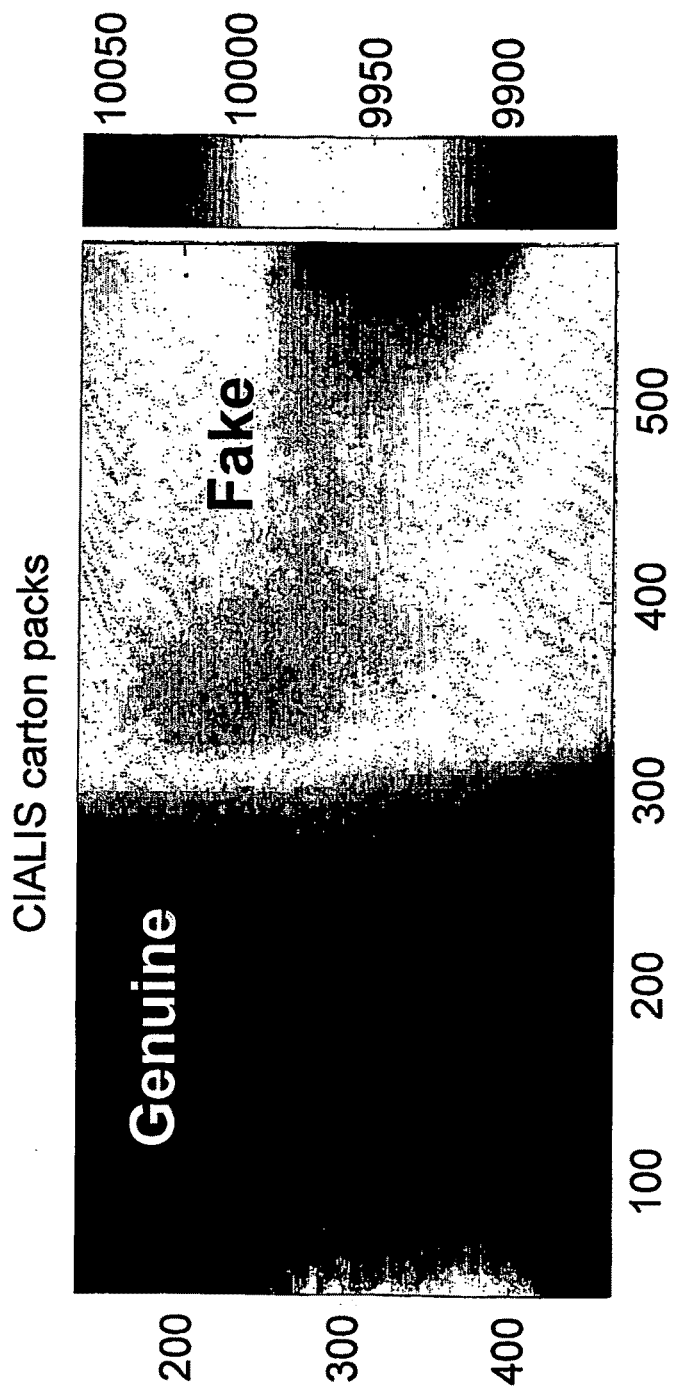
FIG. 7c shows a comparison as obtained by the apparatus of FIG. 7a, between two empty paper carton packages of authentic and counterfeit Cialis pills respectively.

FIG. 7c shows a comparison as obtained by the apparatus, between two empty paper carton packages of authentic and counterfeit Cialis pills respectively. Again, it can be seen that the two images are very easily visually distinguishable.

Figure 7E:
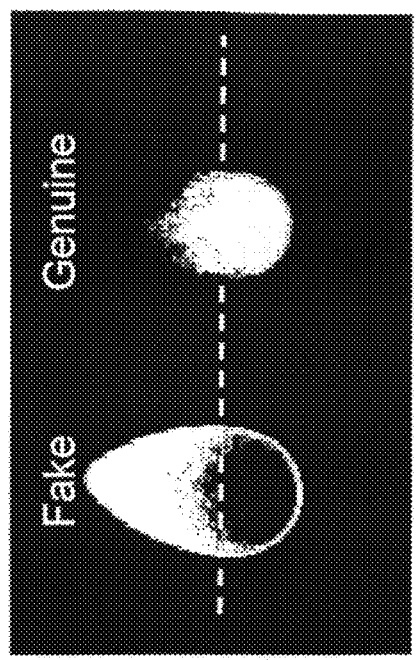
FIG. 7e shows a comparison as obtained by the apparatus, between the two authentic and counterfeit Cialis pills of FIG. 7d.
Figure 7D:
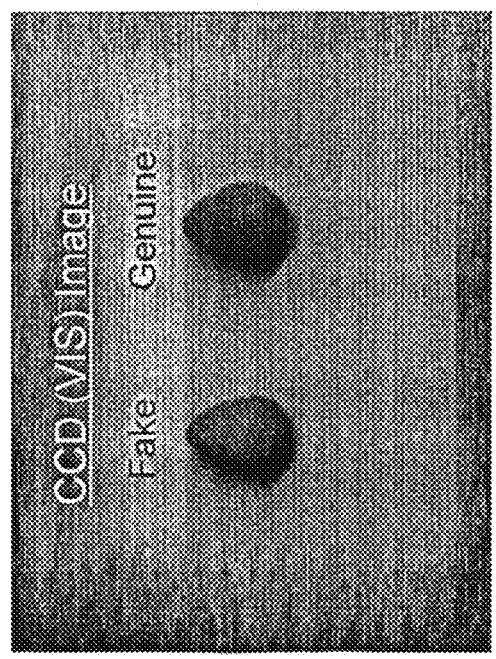
FIG. 7d shows a comparison between the two authentic and counterfeit Cialis pills, as obtained by a CCD (VIS) camera.

FIG. 7d shows a comparison between the two authentic and counterfeit Cialis pills, as obtained by a CCD (VIS) camera. It can be seen that the pills look essentially exactly the same.

FIG. 7e shows a comparison as obtained by the apparatus, between the two authentic and counterfeit Cialis pills of FIG. 7d. It can be seen that the two images are very easily visually distinguishable.

Figure 7G:
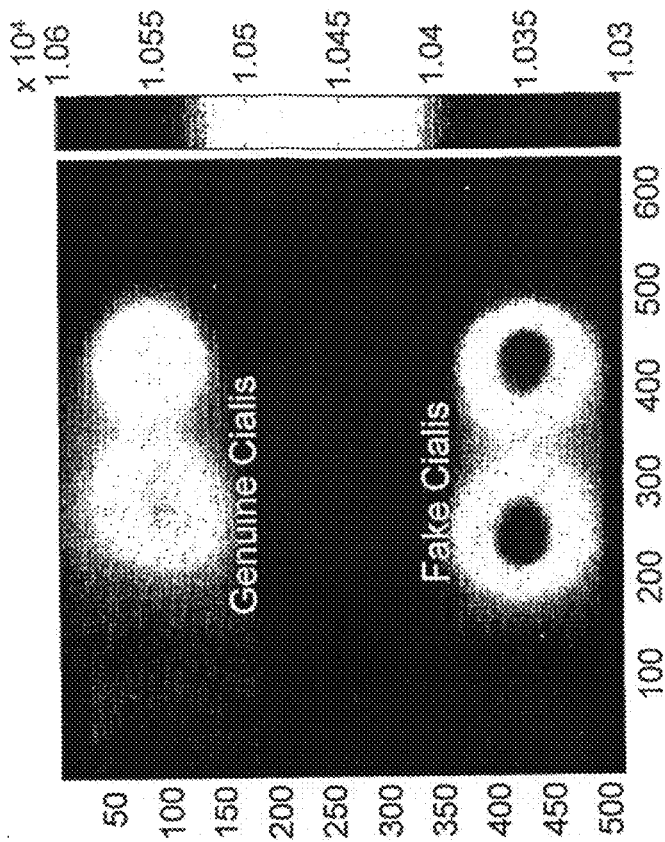
FIG. 7g shows a comparison as obtained by the apparatus, between the two authentic and counterfeit aluminum packages which include the Cialis pills of FIG. 7f.
Figure 7F:
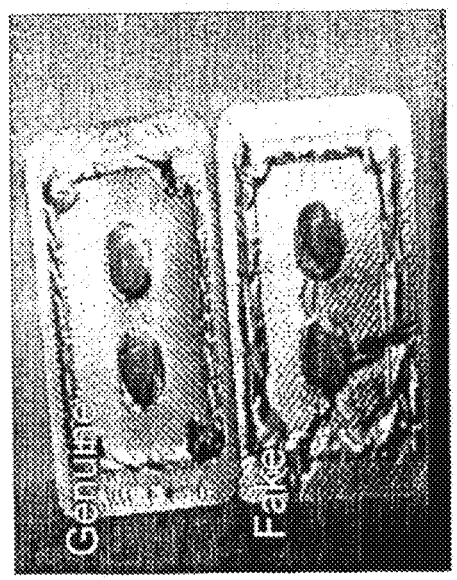
FIG. 7f shows a comparison between the two authentic and counterfeit aluminum packages which include respectively authentic and counterfeit Cialis pills, as obtained by a CCD (VIS) camera.

FIG. 7f shows a comparison between the two authentic and counterfeit aluminum packages which include respectively authentic and counterfeit Cialis pills, as obtained by a CCD (VIS) camera. It can be seen that the packages which include the pills look exactly the same.

FIG. 7g shows a comparison as obtained by the apparatus, between the two authentic and counterfeit aluminum packages which include the Cialis pills of FIG. 7f. It can be seen that the two images are very easily visually distinguishable.

Figures 7H, 7I:
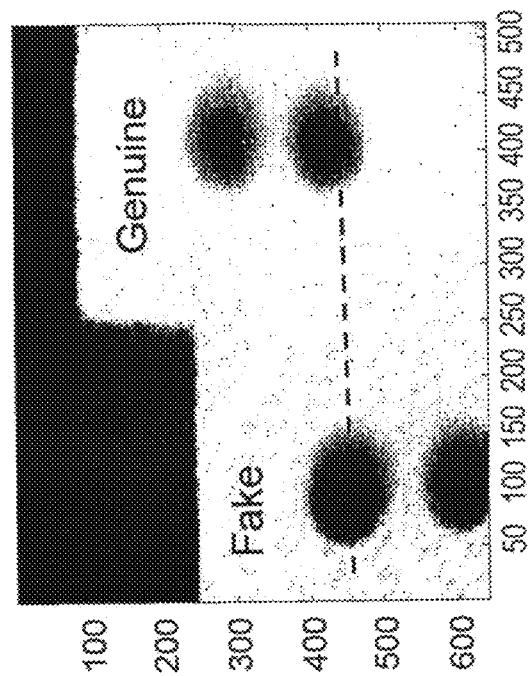
FIG. 7h shows a comparison between two authentic and counterfeit paper cartons which include aluminum packages which in turn each includes respectively authentic and counterfeit Cialis pills, as obtained by a CCD (VIS) camera.
FIG. 7i shows a comparison as obtained by the apparatus of the invention between the two authentic and counterfeit paper carton packages of FIG. 7f, which includes each an aluminum package which in turn includes each authentic and counterfeit Cialis pills respectively.

FIG. 7h shows a comparison between the two authentic and counterfeit paper cartons which include aluminum packages which in turn each includes respectively authentic and counterfeit Cialis pills, as obtained by a CCD (VIS) camera. It can be seen that the packages which include the aluminum packages with pills look exactly the same.

FIG. 7i shows a comparison as obtained by the apparatus of the invention between the two authentic and counterfeit paper carton packages of FIG. 7f, which includes each an aluminum package which in turn includes each authentic and counterfeit Cialis pills respectively. It can be seen that the two images are very easily visually distinguishable.

As said, the example above, as well as several others examples were performed using averaging of several images in order to obtain the signature. It should be noted that other mathematical operations may be used as an alternative to averaging, such as multiplication, integral, differential, division, addition, difference, etc.

EXAMPLE 3

The results of Example 3 were obtained by an apparatus which uses an uncooled detector (in the range of 8 μm to 14 μm). The results were obtained for the same samples as used in Example 2.

Several tests were performed. During the tests, various samples were placed on black body 804. In each of said tests, the black body was initially set to 30° C. After stabilizing the temperature of the black body at 30° C., its temperature was reduced to 15° C., while recording (imaging) every 1 second the emission of the drug during the entire temperature change. The sequence of 10 images that were obtained was averaged to provide a single image as the result of each test. The two authentic and counterfeit images were compared.

Figure 8B:
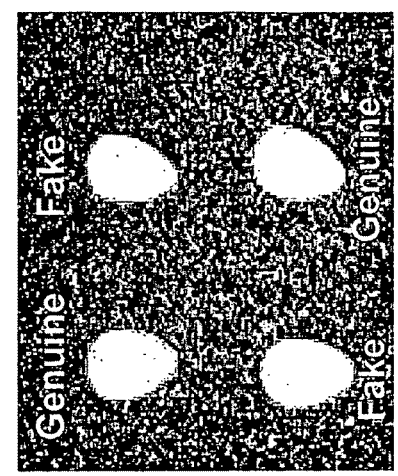
FIG. 8b shows the two authentic images and two counterfeit images of the Cialis pills of FIG. 8a, as obtained by a CCD (VIS) camera.
Figure 8A:
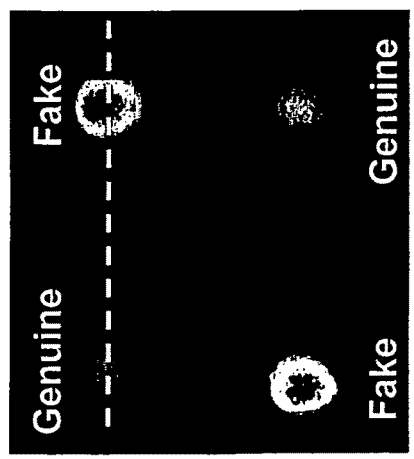
FIG. 8a shows a comparison as obtained by the uncooled apparatus between the two authentic and two counterfeit Cialis pills respectively.

FIG. 8a shows a comparison as obtained by the uncooled apparatus between the two authentic and two counterfeit Cialis pills respectively. It can be seen that the authentic and counterfeit images are very easily visually distinguishable.

FIG. 8b shows the two authentic images and two counterfeit images of the Cialis pills of FIG. 8a, as obtained by a CCD (VIS) camera. It can be seen that all said pills images look exactly the same.

Figure 8C:
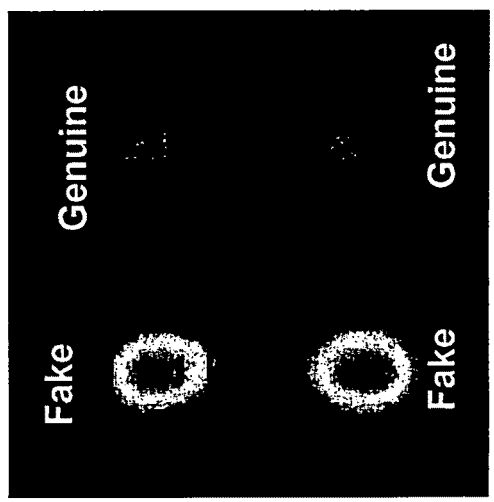
FIG. 8c shows a comparison as obtained by an uncooled apparatus between two fully packed (paper carton and aluminum) authentic Cialis pills and two fully packed counterfeit Cialis pills respectively.

FIG. 8c shows a comparison as obtained by the uncooled apparatus, between two fully packed (paper carton and aluminum) authentic Cialis pills and two fully packed counterfeit Cialis pills respectively. It can be seen that the respective authentic and counterfeit images are very easily visually distinguishable.

It is known in the art that an uncooled detector is much cheaper than a cooled detector. It has been found by the inventors that the results by the two types of detectors are essentially the same. In other words, both provide very distinguishable results.

In still another embodiment, both cooled MWIR detector and uncooled LWIR detector are used together in the same system. Such multi spectral detector use can give a higher range of sensitivity. Although such a system is more expensive and complicated than of a single detector system, a multi spectrum system is advantageous in some hard to distinguish cases.

EXAMPLE 4

In Example 4, an apparatus which having an InSb (in the range of 3 μm to 5.4 μm) cooled detector (640×512 pixels at 15 μm pitch) was used.

A test was performed with an authentic container of Optalgin. drops and another with a counterfeit container of a liquid Optalgin. During the tests, the samples were placed on a black body. In each of said tests, the black body was initially set to 30° C. After stabilizing the temperature of the black body at 30° C., its temperature was reduced to 15° C., while recording every 1 second the emission of the drug during the entire temperature change. The sequence of 10 images that were obtained was averaged to provide a single image for each test. The two authentic and counterfeit images were compared.

FIG. 9a shows an image of authentic and counterfeit liquid Optalgin containers, as obtained by a CCD (VIS) camera. The upper container in the image is authentic, and the lower is counterfeit. FIG. 9b shows the same containers respectively, as obtained by said apparatus, as a result of the experiment as described. As can be seen, these two images of the authentic and counterfeit containers are very easily visually distinguishable.

While some embodiments of the invention have been described by way of illustration, it will be apparent that the invention can be carried into practice with many modifications, variations and adaptations, and with the use of numerous equivalents or alternative solutions that are within the scope of persons skilled in the art, without exceeding the scope of the claims.

The invention claimed is:

1. A method for determining the authenticity of a pharmaceutical product comprising:
   (a) actively cooling said product to a temperature below ambient temperature;
   (b) acquiring, in a wavelength or wavelength spectrum selected from the mid wave IR (MWIR) to very long wave IR (VLWIR) spectrum, one or more thermographic IR images of said product, at least one image being acquired while the temperature of the product is below ambient temperature;
   (c) comparing said acquired one or more images of said product or a quantified value deduced therefrom with a signature of a reference drug; and
   (d) displaying said comparison thereby enabling determination of the authenticity of said product.

2. The method of claim 1, comprising placing said product on a cooling source or within a cooling chamber and cooling said product while on or within said cooling source.

3. The method of claim 1, wherein the cooling of the product comprises applying a cooling pulse onto said product.

4. The method of claim 1, wherein said one or more IR images are acquired at times during or following said cooling.

5. The method of claim 1, comprising processing said one or more IR images of said product into a visual image or a quantified value.

6. The method claim 1, wherein said comparison comprises correlating between the visual image or quantified value of the acquired one or more IR images of the product with said signature of to reference drug.

7. The method of claim 6, wherein said signature of a reference drug comprises a visual image or quantified value from a database of visual images or quantified values of a plurality of reference drugs.

8. The method of claim 1, comprising displaying said comparison, wherein said displaying comprises displaying one or more visual images of said product alongside with one or more images of said reference drug.

9. The method of claim 7, wherein said database comprises a plurality of signatures of reference drugs comprising at least one intentionally introduced distinguishing sign capable of being imaged by said thermography apparatus.

10. A system for determining the authenticity of a pharmaceutical product comprising:
- a cooling source for cooling said pharmaceutical product to a temperature below ambient temperature;
- a thermography Infra Red (IR) apparatus for acquiring, in a wavelength or a wavelength spectrum selected from the mid wave IR (MWIR) to very long wave IR (VLWIR) spectrum one or more thermographic IR images of said product, at least one image being acquired while the temperature of the product is below ambient temperature;
- a database of signatures of reference drugs; and
- a display unit for displaying at least said one or more IR images and a signature of a reference drug, or for display of a result of comparison between said one or more IR images and said signature of a reference drug.

11. The system of claim 10, wherein said signature of a reference drug is retrieved from said database.

12. The system of claim 10, comprising a memory carrying said database.

13. The system of claim 10, wherein said cooling source is adapted to apply a cooling pulse onto said product for a time period sufficient to allow cooling of said product below ambient temperature, and said thermography IR apparatus is configured to acquire one or more IR images at times during or following said cooling.

14. The system of claim 10, comprising a comparison unit for comparing between said acquired one or more IR images of said product and a signature of a reference drug, said comparison unit comprises a processing unit adapted to receive the one or more acquired IR images from the thermography IR apparatus and process said one or more images into a visual image or a quantified value comparable with said signature of a reference drug.

15. The system of claim 14, wherein said comparison unit is adapted to process said one or more acquired IR images in comparison with a signature of a reference drug.

* * * * *

UNITED STATES PATENT AND TRADEMARK OFFICE
CERTIFICATE OF CORRECTION

PATENT NO. : 8,586,928 B2  
APPLICATION NO. : 12/672593  
DATED : November 19, 2013  
INVENTOR(S) : Sinbar et al.

Page 1 of 1

It is certified that error appears in the above-identified patent and that said Letters Patent is hereby corrected as shown below:

In the Claim

In claim 6, at column 18, line 61, please change "to" to --a--.

Signed and Sealed this  
Seventh Day of January, 2014

Margaret A. Focarino  
*Commissioner for Patents of the United States Patent and Trademark Office*